United States Patent [19]

Brindak

[11] E Patent Number: Re. 33,468

[45] Reissued Date of Patent: Dec. 4, 1990

[54] PROCESS AND APPARATUS FOR TESTING FLUIDS FOR FOULING AND ANTIFOULANT PROTOCOL

[75] Inventor: Nicholas J. Brindak, Auburn, N.Y.

[73] Assignee: Drew Chemical Corporation, Boonton, N.J.

[21] Appl. No.: 323,746

[22] Filed: Feb. 17, 1989

Related U.S. Patent Documents

Reissue of:

[64] Patent No.: 4,346,587
Issued: Aug. 31, 1982
Appl. No.: 202,352
Filed: Oct. 30, 1980

[51] Int. Cl.[5] ..... G01N 17/00

[52] U.S. Cl. ..... 73/61.200

[58] Field of Search ..... 73/61.2, 86; 422/53; 436/6

[56] References Cited

U.S. PATENT DOCUMENTS

| | | | |
|---|---|---|---|
| 1,807,446 | 5/1931 | Smeby | 137/625.37 |
| 2,596,305 | 5/1952 | Stevens | 73/292 |
| 3,141,324 | 7/1964 | Boies et al. | 73/61.2 |
| 3,250,117 | 5/1966 | Dajani | 73/61.2 |
| 3,361,150 | 1/1968 | Horner | 204/404 |
| 3,488,996 | 1/1970 | Pfrehm | 73/62.1 R |
| 3,555,901 | 1/1971 | Delatorre et al. | 73/197 |
| 3,592,212 | 7/1971 | Schleimer | 137/93 |
| 3,633,420 | 1/1972 | Holzem | 73/199 |
| 3,730,685 | 5/1973 | Prohaska | 436/51 |
| 3,803,912 | 4/1974 | Ohno | 73/195 |
| 3,848,187 | 11/1974 | Rohrback et al. | 324/65 CR |
| 3,913,378 | 10/1975 | Hausler | 73/61.2 X |
| 3,918,300 | 11/1975 | Weisstuch et al. | 73/112 |
| 4,024,751 | 5/1977 | Potrzebowski | 374/43 |
| 4,098,662 | 7/1978 | Schell et al. | 204/404 |
| 4,100,799 | 7/1978 | Bradham, III et al. | 73/197 |
| 4,103,161 | 7/1978 | Thomasson | 73/195 X |
| 4,106,331 | 8/1978 | Bunton et al. | 73/61.1 R |
| 4,138,878 | 2/1979 | Holmes et al. | 73/61.2 X |
| 4,168,624 | 9/1979 | Pichon | 73/19 X |
| 4,176,544 | 12/1979 | Eyles et al. | 73/61.2 |
| 4,181,347 | 1/1980 | Clark | 378/199 |
| 4,217,544 | 8/1980 | Schmidt | 324/65 CR |
| 4,383,908 | 5/1983 | Phelps et al. | 204/409 |
| 4,449,746 | 5/1984 | Clark | 378/208 |

FOREIGN PATENT DOCUMENTS 1396378 6/1975 United Kingdom .

OTHER PUBLICATIONS

Nishioka, "Automated in-situ Water Quality Monitoring", *Advances in Instrumentation*, vol. 33, No. 3, 1978.
"On Stream Desludging", *The Betz Indicator*, vol. 36, No. 5, 1967.
"Travelab", *The Betz Indicator*, vol. 39, No. 5, 1970.
"Travelab", *Brochure 718*, 1974.
Fischer, "Fouling Measurement", *Chemical Engineering Progress*, vol. 71, No. 7, 1975.

(List continued on next page.)

*Primary Examiner*—Hezron E. Williams
*Assistant Examiner*—Joseph W. Roskos
*Attorney, Agent, or Firm*—Pollock, Vande Sande & Priddy

[57] ABSTRACT

There is disclosed a novel mobile apparatus and process therefor including a heat transfer test assembly and related conduit and valve assemblies for connection in fluid flow communication to a heat transfer apparatus for in-situ testing and generation of foulant data to permit substantially simultaneous implementation of the antifoulant protocol of the fluid passing therethrough and including monitoring and recording apparatus together with a source of antifoulants for controlled introduction into the fluid. The heat transfer test assembly includes a heating member for controlled heat input and thermocouples to measure the wall temperature of the heating member to permit fouling determinations at varying flow rates with simultaneous monitoring and recording thereof together with data, such as corrosion, pH, conductivity, and the like. The heat transfer test assembly is placed in fluid communication with a source of antifoulants of controlled dosage with concomitant evaluation of efficaciousness of the antifoulant protocol on the fluid.

21 Claims, 1 Drawing Sheet

OTHER PUBLICATIONS

Welder et al., "Dynamic Deposit Monitor—A Unit for Determining the Rate of Deposit Buildup in Cooling Systems and Evaluating Inhibitor Performance", presented at the 36th Annual Meeting, International Water Conference, Nov. 1975 (paper No. IWC-No. 75-3).

Knudsen et al., "The Effect of Heat Transfer Surface Temperature on the Scaling Behavior of Simulated Cooling Tower Water", 1978.

Knudsen, "Apparatus and Technique for Measurement of Fouling of Heat Transfer Surfaces", *EPRI Seminar*, Mar. 25-29, 1979.

Composite Catalog, 1976-77, p. 239.

Knudsen and Herman, "The Use of a Novel Portable Fouling and Corrosion Monitor-Recorder in Industrial Cooling Water Systems" (Paper IWC-No. 38) Nov. 1, 1979.

PROCESS AND APPARATUS FOR TESTING FLUIDS FOR FOULING AND ANTIFOULANT PROTOCOL

Matter enclosed in heavy brackets [ ] appears in the original patent but forms no part of this reissue specification; matter printed in italics indicates the additions made by reissue.

FIELD OF INVENTION

The present invention relates to a process and apparatus for testing fluids, and more particularly, to a process and apparatus for the in-situ testing and generation of foulant data together with antifoulant protocol.

BACKGROUND OF THE INVENTION

The chemical water treatment industry has historically been involved with reducing or inhibiting the inherent scale forming or fouling tendencies of natural waters associated with large industrial cooling water systems. Many of the foulant components found in water systems originate with the incoming supply, but some contaminants enter the system from the local environment or from process contamination.

Fouling is an extremely complex phenomenon. From a fundamental point of view, it may be characterized as a combined momentum, heat and mass transfer problem. In many instances, chemical reaction kinetics is involved, as well as solubility characteristics of salts in water and corrosion technology. It has been stated that if the fouling tendency of a cooling water can be accurately predicted before a plant is designed and built, significant capital savings might be realized through more accurate heat exchanger specifications.

Usually, it is a normal practice to increase heat exchanger surface area to overcome losses in performance caused by fouling deposits with such additional surface area often accounting for more than half of the actual surface are of the heat exchanger. When such design practice is employed with titanium, stainless steel and like expensive materials of construction, it can be appreciated that capital expenditures might be significantly reduced if data could be developed to anticipate and provide for an antifoulant protocol.

Fouling of a heat transfer surface is defined as the deposition on a surface of any material which increases the resistance to heat transfer. The fouling tendency of a fluid in contact with a heat transfer surface is a function of many variables including the components of the fluid, which in the case of water include, inter alia, crystals, silt, corrosion products, biological growths, process contaminates, etc. Generally, deposits are comprised of a combination of several of these materials in relationship to, inter alia, the geometry of the heat transfer surface, materials of construction, temperature, etc. and thus, chemical inhibitors to solve the problem of a particular deposit involves a variety of different chemicals introduced at varying concentration and at varying times.

Industry has been relegated to the use of laboratory simulators or time lapse evaluations of process heat exchangers and test heat exchangers with the requirement that such equipment is taken off line, shut down, opened and inspected to evaluate fouling problems and antifoulant protocols. In the case of process heat exchangers, such inspection usually results in significant plant down time and lost production. Evaluation covers the entire period of process operation and shows accumulated results, which include system upsets, process leaks, the loss of chemical feed or human errors. While the sampling and laboratory testing of fluids permits evaluation of the fluids, the results of laboratory testing are tedious and do not provide results of simultaneous evaluation.

OBJECTS OF THE PRESENT INVENTION

An object of the present invention is to provide novel process and apparatus for in-situ testing and generation of foulant data to permit substantially simultaneous implementation of antifoulant protocol.

Another object of the present invention is to provide novel process and apparatus for facile connection to an on-line unit or process heat exchanger for in-situ testing and generation of foulant data to permit substantially simultaneous implementation of antifoulant protocol to the fluid.

Still another object of the present invention is to provide a novel process and apparatus for in-situ on-stream testing and generation of foulant data to permit substantially simultaneous implementation of the antifoulant protocol to the fluid with continued generation of foulant data to ascertain efficaciousness of the antifoulant protocol.

A still further object of the present invention is to provide a novel process and apparatus for in-situ on stream testing of fluids and generation of foulant data to permit substantially simultaneous implementation of antifoulant protocol and the continuous monitoring of antifoulant protocol.

Still another object of the present invention is to provide a novel process and apparatus for in-situ testing and generation of foulant data to permit substantially simultaneous implementation of the anti-foulant protocol for unit or process heat transfer equipment and readily movable throughout a plant complex and from plant to plant.

SUMMARY OF THE INVENTION

These and other objects of the present invention are achieved by a novel mobile apparatus and process therefor including a heat transfer test assembly and related conduit and valve assemblies for connection in fluid flow communication to a heat transfer apparatus for in-situ testing and generation of foulant data to permit substantially simultaneous implementation of the antifoulant protocol of the fluid passing therethrough and including monitoring and recording apparatus together with a source of antifoulants for controlled introduction into the fluid. The heat transfer test assembly includes a heating member for controlled heat input and thermocouples to measure the wall temperature of the heating member to permit fouling determinations at varying flow rates with simultaneously monitoring and recording thereof together with data, such as corrosion, pH, conductivity, and the like. The heat transfer test assembly is placed in fluid communication with a source of antifoulants of controlled dosage with concomitant evaluation of efficaciousness of the antifoulant protocol on the fluid.

BRIEF DESCRIPTION OF THE DRAWINGS

Further objects and advantages of the present invention will become apparent upon consideration of the detailed disclosure thereof, especially when taken with the accompanying drawings wherein like numerals designate like parts throughout and wherein:

FIG. 3 is a schematic diagram of the process and apparatus for continuously testing, monitoring and recording data relative to the heat transfer test assembly as well as for monitoring and recording data as to corrosion, conductivity, pH, and the like.

DETAILED DESCRIPTION OF THE PRESENT INVENTION

Figure 1:
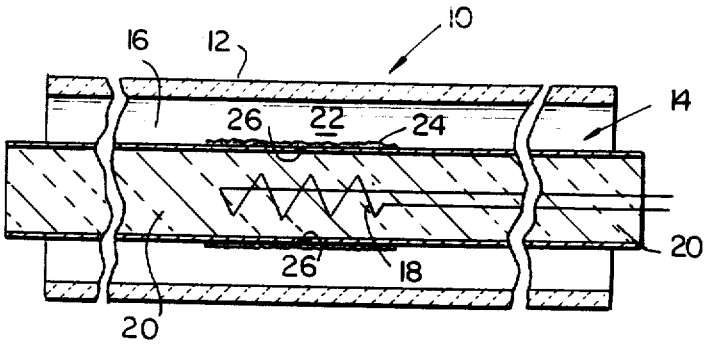
FIG. 1 is a cross-sectional elevational view of the heat transfer test assembly.

Referring now to FIG. 1, there is illustrated a heat transfer test assembly, generally indicated as 10, and comprised of a tube member 12 and an inner cylindrically-shaped heating member, generally indicated as 14, formed of a tube member 16 in which a high resistant heating element 18 is embedded within an insulating matrix 20, such as magnesium oxide. The heating member 14 is coaxially positioned within the tube member 12 to form an annular fluid flow passageway 22. Symmetrically disposed in the tube member 16 of the heating member 14 is a plurality of surface thermocouples 26 generally disposed at positions corresponding to the hour hand at 3,6,9 and 12 o'clock for sensing wall temperature.

The tubular member 12 is formed of any suitable transparent material, such as glass to permit visual observation of flow as well as scale formation 24 about the surface of the heating member 14. The tube member 16 of the heating member 14 is formed of a metallic material, such as stainless steel, copper, titanium, mild steel, admiralty metal or the like, dependent on the fluid to be initially tested by passage through the test member 10 or in the case of existing units of a like metallic material as that in the unit. Normally, stainless steel is used for normal cooling water application whereas admiralty metal is employed for sea water and brackish water applications.

As more fully hereinafter described, the fouling tendency of a fluid may be evaluated by the passage of a fluid through the heat transfer test assembly 10 under controlled rates of flow and heat output from the heating element 18 through measurement of temperature drops ($\Delta ts$) between the tube member 16 and the fluid to permit a determination of the resistance (R) of the scale formation 24 therefor.

Figure 2:
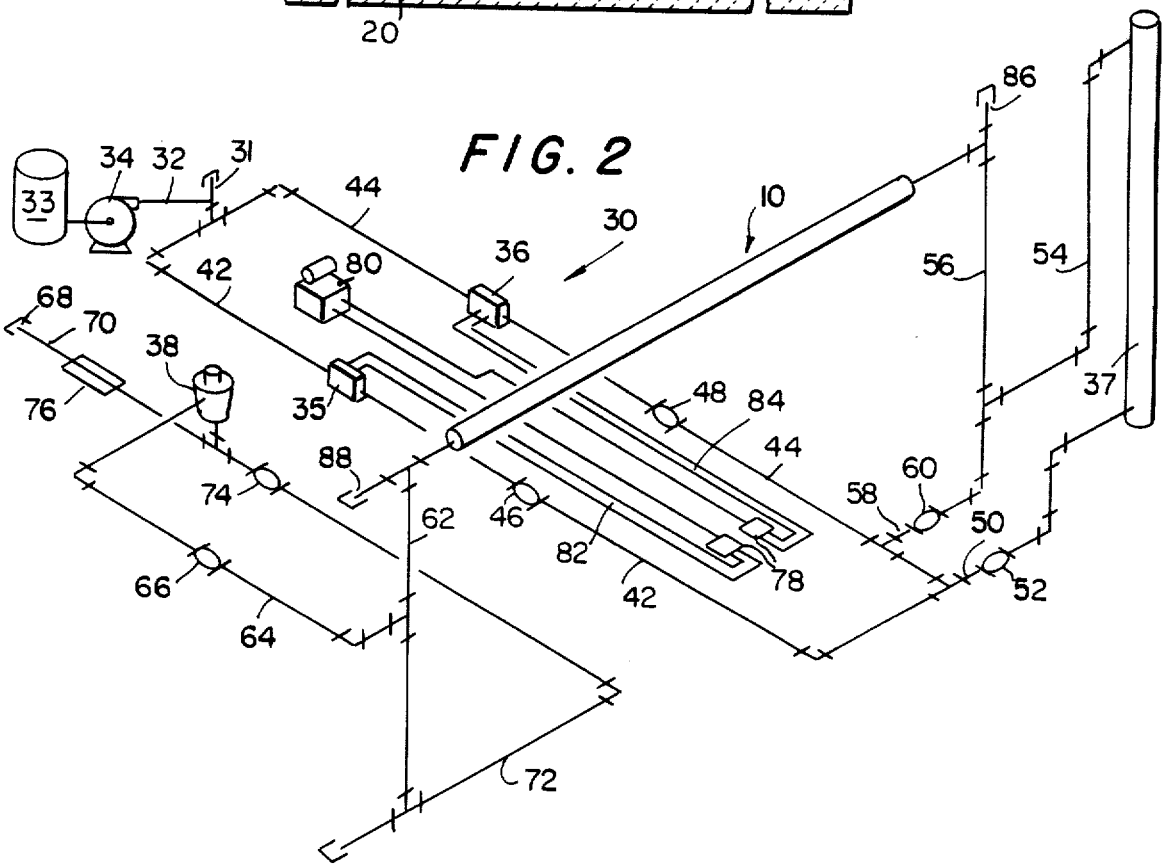
FIG. 2 is a piping diagram of the novel process and apparatus of the present invention including the heat transfer test assembly.

The heat transfer test assembly 10 is positioned within a piping assembly, generally indicated as 30 referring now to FIG. 2, including an inlet conduit 31 and an antifoulant conduit 32 in fluid communication with a container 33 including an antifoulant via the discharge side of a pump 34. The piping assembly 30 includes flow meters 35 and 36, a rotameter 37 and a flow rate control valve 38. The inlet conduit 31 is in parallel flow communication with the flow meters 35 and 36 by conduits 42 and 44 under the control of valves 46 and 48, respectively. Conduits 42 and 44 are in fluid flow communication by conduit 50 under the control of an isolation valve 52 with one end of the rotameter 37 with the other end of the rotameter 37 being in fluid flow communication by conduits 54 and 56 with the inlet end of the heat transfer test [section] *assembly* 10. Conduit 44 is in fluid flow communication by conduit 58 under the control of by-pass valve 60 with conduit 56.

The outlet of the heat transfer test assembly 10 is in fluid flow communication by conduit 62 and conduit 64 under the control of an isolation valve 66 via the flow rate control valve 38 to outlet 68 by conduit 70. Conduit 62 is in fluid flow communication with conduit 70 by conduit 72 under the control of a by-pass valve 74. The conduit 70 is provided with flow cell 76 including a plurality of probes (not shown) to measure other parameters of the fluid, as more fully hereinafter discussed.

The flow meters 35 and 36 are preferably of the venturi type with each flow meter having a different design rating of flow rates and are electrically connected via transducers 78 to a differential pressure cell 80 and by lead lines 82 and 84, respectively, to sense the pressure drop across the flow meters 35 and 36. The piping assembly 30 is provided with a thermocouple 86 to monitor the bulk inlet water temperature and with a high temperature cutoff 88.

In order to provide sufficient range of flow velocities, a plurality of heat transfer test assemblies 10 of differing diameters may be used for interchangeable insertion into the piping assembly 30. The flow rate control valve 38 is preferably of the constant flow type with an internal pressure equalizer (not shown) to insure flow at the preselect [valve] *value*. The rotameter 37 permits visual monitoring and may be electronically monitored by a differential pressure cell (not shown).

Figure 3:
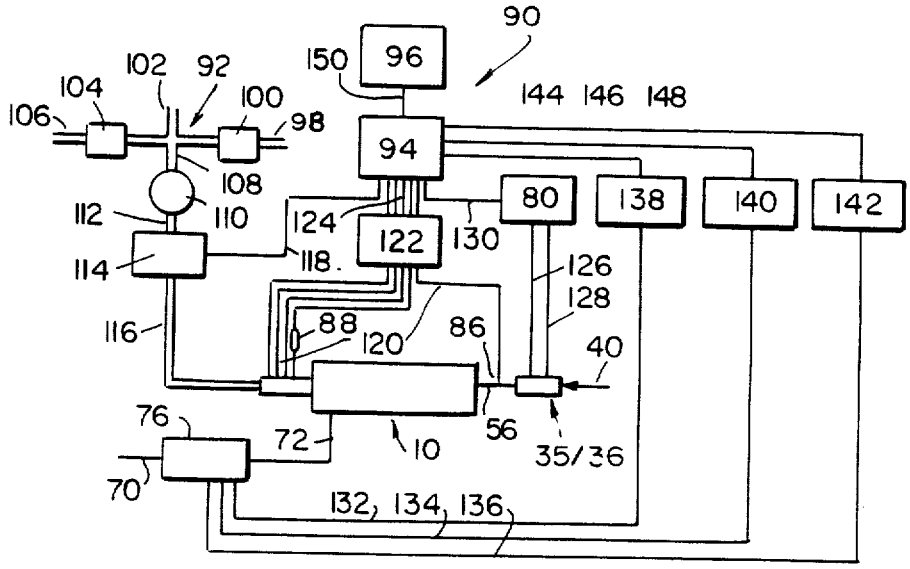

The piping assembly 30 is integrated or coupled with a monitoring and recording assembly, generally indicated as 90, including components of the piping assembly 30, referring now to FIG. 3, disposed on a support structure (not shown) for positioning within a mobile container (not shown), such as a trailer, van or the like, for facile movement from location to location to test a fluid passing through a unit such as a heat exchanger, reactor or the like, as more fully hereinafter discussed. The container is provided with environment capabilities to provide pre-select conditions of temperature, humidity and the like to insure proper functioning of the various units of the monitoring and recording assembly.

The monitoring and recording assembly 90 includes a power inlet assembly, generally indicated as 92, an analog to digital converter 94 and a computer print-out assembly 96. The power inlet assembly 92 is comprised of a 110 Vac. inlet connector 98 including transformer 100, a 220 Vac. inlet connector 102 and a 440 Vac. inlet connector 104 including a transformer 106 connected by leads 108 to a variable rheostat 110. Generally, 110 Vac. is utilized for the environmental capabilities with one of the other power sources utilized in the monitoring and recording capabilities. The variable rheostat 110 is connected by leads 112 to a wattmeter transducer 114 providing a source of power by leads 116 for the heating element 18 of the tube member 16.

The wattmeter transducer 114 generates a signal transmitted via lead 118 to the analog-digital converter 94 representative of the power level of the heating element 18 of the tube member 16. The thermocouples 26 and 86 generate signals representative of a temperature transmitted via lines 120 to a reference junction 122 for transmission via leads 124 to the analog-digital converter 94.

The transducers 78 [receiving] *receive* signals generated by the flow meters 35 and 36 and in turn transmits a signal via leads 126 and/or lead 128 to differential pressure cell 80 which generates an analog signal representative of flow rate transmitted by lead 130 to the analog-digital converter 94.

The flow cell 76 including a plurality of probes are connected by leads 132, 134 and 136 to a conductivity monitor 138, a pH monitor 140 and a corrosion monitor 142, respectively, connected to the analog-digital converter 94 by leads 144, 146 and 148, respectively. As known to one skilled in the art, the analog-digital converter transforms analog information into digital output data, which in turn is transmitted by lead 150 to the computer printout assembly 152 for recording in a referenced time frame.

In operation, the monitoring and recording assembly 90 disposed on a suitable support assembly and enclosed in a self-contained environmental container is caused to be positioned adjacent a unit operation or process such as a heat exchanger or delignification digester, respectively, employing a fluid to be tested, inter alia, for fouling tendencies to permit evaluation and develop an antifoulant protocol. A source of power is connected to the power inlet assembly 92 and a flexible conduit placed in fluid flow communication with the unit operation or process, generally on the up-stream side thereof. The circulating fluid is caused to flow via conduit 31 into the piping assembly 30 via either flow meter 35 or 36 by control of valves 46 or 48, respectively, and thence sequentially through the rotameter 37 via conduit 50 under the control of valve 52, through the heat transfer test assembly 10 via conduits 54 and 56, through the flow rate control valve 38 via conduit 62 and conduit 64 under control of valve 66 and finally through the flow cell 76 via conduit 70 to be discharged through outlet 68 to waste or to be returned to the unit operation or process.

During such operational time period, power is supplied by leads 116 to the heater element 18 of the tube member 16 with the temperature of the wall of the heating member 14 being monitored to obtain an average temperature thereof. Simultaneously, the bulk fluid temperature is monitored by thermocouple 86 together with the monitoring of the fluid velocity to determine what, if any, velocity effects there are on fouling under given operating conditions. Water velocity is controlled by the constant flow valve 38 and is visually monitored by the rotameter 37 concomitant with electronic monitoring by the differential pressure cell 80 sensing the pressure drop across either flow meter 35 or 36.

The wall thermocouples 26, the bulk water temperature thermocouple 86, the wattmeter transducer 114 and differential pressure cell 80 are connected to the analog-coverter 94 via reference junctions 122 to convert analog electrical signals to digital output signals which are transmitted for recordation to the computer printer 96, it being understood that the computer printer is capable of effecting some computation to generate calculated data, such as a fouling factor. Such fouling factor is time related to data from the conductivity monitor 138, the pH monitor 140 and the corrosion monitor 142.

Thereafter, the pump 34 is energized for a predetermined time period or continuously to quantitatively introduced antifoulant into the piping assembly with concomitant monitoring of the hereinabove factors together with concomitant generation of fouling to evaluate the efficacy of the antifoulant protocol. Monitoring and evaluation of the antifoulant protocol as well as changes thereto permit the evaluation of a finalized antifoulant protocol for a given aqueous or nonaqueous fluid system. Accordingly, the antifoulant treated fluid may be returned via the discharge conduit 70 to the unit operation or unit process thereby permitting constant evaluation of the antifoulant protocol for the unit operation or unit process.

The following example is included for the purpose of illustrating the invention and it is to be understood that the scope of the invention is not to be limited thereby.

EXAMPLE

Cooling water for a gas processing plant having a pH of from 7.2 to 7.6 treated with 25 ppms of antifoulant chemicals including a combination of phosphonates, aromatic glycols and chelating agents generated a fouling factor of from 240 to 260. In addition to the antifoulant chemicals, there is introduced 150 ppms of a corrosion inhibitor and 10 ppms of a microbiocides (on a shock basis to the cooling water).

An antifoulant protocol is developed whereby there is added 150 ppms of a corrosion inhibitor, 50 ppms of a non-ionic antifoulant and 50 ppms of a microbiocide together with a base to alter the range of pH to from 7.8 to 8.2. The effects of the new protocol are determined by continued operation of the heat transfer test [section] *assembly* 10 under like conditions whereby the resulting fouling factor is from 20 to 25, a ten fold reduction from that originally observed.

After completion of the development of an antifoulant protocol, the monitoring and recording assembly 90 is disconnected from the unit operation or process by closing valves 46 or 48 and disconnecting inlet 40 from the fluid source. Thereafter, the monitoring and recording assembly 90 may be facilely moved to another location within the plant or to another plant site.

The process and apparatus of the present invention is particularly suited in the development of antifoulant protocols for once through cooling systems, chemical processing, such as a Kamyr digester, or process water for condensers.

While the process and apparatus of the present invention has been described generally in the context of an aqueous heat transfer fluid circulating through a heat exchanger, it will be understood that the process and apparatus is applicable to any heat transfer fluid including hydrocarbons, euthetic salt solutions and the like, circulating through a vessel in heat transfer relationship where fouling is a problem.

While the present invention has been described in connection with the exemplary embodiment thereof, it will be understood that many modifications will be apparent to those of ordinary skill in the art; and that this application is intended to cover any adaptations or variations thereof. Therefore, it is manifestly intended that this invention be only limited by the claims and the equivalents thereof.

What is claimed:

1. An apparatus for testing a fluid to generate fouling data and other parameters to develop an antifoulant protocol for said fluid, which comprises:

a piping assembly including fluid inlet and outlet [means] and a heat transfer test assembly, said heat transfer test assembly including a heating member including a heating element disposed within a conduit [means] having a passageway for said fluid;

means for measuring temperature of said fluid entering said heat transfer test assembly;

means for supplying electrical energy of a pre-select quantity to said heating element;

means for measuring wall temperature of said heating [element] *member;* flow means for measuring velocity of said fluid through said conduit [means];

means for generating fouling data from said pre-select quantity of electrical energy supplied to said heating element, said *velocity of said fluid, said* measured temperature of said fluid and said measured wall temperature of said heating member; and means for introducing an antifoulant into said fluid.

2. The apparatus as defined in claim 1 and further comprising a flow control valve *connected in said piping assembly.*

3. The apparatus as defined in claim 2 wherein said flow control valve is of a constant flow type including a pressure equalizer.

4. The apparatus as defined in claim 1 wherein said flow means includes a venturi device.

5. The apparatus as defined in claim 4 wherein said venturi device is connected to a differential pressure cell to generate a signal responsive to a pressure drop across said venturi device.

6. The apparatus for testing a fluid as defined in claim 1 and further including two flow means of differing rated flow rates.

7. The apparatus as defined in claim 1 and further including converter means to convert analog electric signals to digital output signals.

8. The apparatus as defined in claim 1 wherein said apparatus is supported on a movable structure within a chamber having environmental regulating capabilities.

9. The apparatus as defined in claim 8 wherein said movable structure is a van.

10. The apparatus as defined in claim 1 and further comprising means to disable said means for supplying electrical energy to said heating element at a pre-select elevated temperature condition.

11. A process for testing a fluid to be passed through a unit in an indirect heat transfer relationship to develop an antifoulant protocol for said fluid, which comprises:

(a) connecting said unit in fluid flow communication with a test zone of a mobile assembly, said test zone including a heating member having a source of heat;

(b) measuring a temperature of said fluid;

(c) providing source of heat with a pre-select quantity of electrical energy;

(d) measuring wall temperature of said heating member during passage of said fluid through said test zone;

(e) measuring a flow rate of said fluid;

(f) generating fouling data *from said pre-select quantity of electrical energy, said flow rate, said temperature of said fluid and measured wall temperature;* and (g) introducing an antifoulant into said fluid while continuing steps (b) to (e).

12. The process as defined in claim 11 wherein the quantity and kind of antifoulant is varied to develop said antifoulant protocol.

13. The process as defined in claim 11 wherein said flow rate is measured by a differential pressure across a venturi zone.

14. The process as defined in claim 11 wherein said flow rate of said fluid is varied through said test zone.

15. The process as defined in claim 11 wherein said data is also recorded in a manner for further electronic transmissions to a data bank for such unit.

16. The process as defined in claim 11 wherein said unit is on stream.

17. The process as defined in claim 15 wherein said fluid after passage through said test zone is continuously recycled to said unit.

18. The process as defined in claim 11 wherein steps (b) to (e) *each* generate [d] analog signal, *which signals are then* [convertable] *converted* to [a] digital signals which [is] *are* recorded together with said fouling data.

*19. The apparatus of claim 1 which further includes: means for measuring said other parameters including corrosion, pH and conductivity of said fluid.*

*20. The apparatus of claim 19 which further includes means for recording said fouling data and said other parameters.*

*21. The process of claim 18 which further comprises: means for measuring corrosion, pH and conductivity of said fluid and wherein measurements of corrosion, pH and conductivity are recorded along with said fouling data.*

* * * * *

UNITED STATES PATENT AND TRADEMARK OFFICE

CERTIFICATE OF CORRECTION

PATENT NO. : RE 33,468

DATED : Dec. 4, 1990

INVENTOR(S) : Brindak

It is certified that error appears in the above-identified patent and that said Letters Patent is hereby corrected as shown below:

Col. 8, line 41, "means for" should be deleted.

Signed and Sealed this

Seventeenth Day of August, 1993

Bruce Lehman

*Attest:*

BRUCE LEHMAN

*Attesting Officer*

*Commissioner of Patents and Trademarks*